(12) United States Patent
Benamou et al.

(10) Patent No.: US 8,597,287 B2
(45) Date of Patent: Dec. 3, 2013

(54) METHOD AND SYSTEM FOR VARYING OUTPUT INTENSITY OF ENERGY APPLIED TO AN ELECTROSURGICAL PROBE

(75) Inventors: Steffan A. Benamou, San Jose, CA (US); Brannon P. Wells, San Jose, CA (US); Saheel B. Sutaria, Mountain View, CA (US)

(73) Assignee: Stryker Corporation, Kalamazoo, MI (US)

( * ) Notice: Subject to any disclaimer, the term of this patent is extended or adjusted under 35 U.S.C. 154(b) by 695 days.

(21) Appl. No.: 12/658,300

(22) Filed: Feb. 9, 2010

(65) Prior Publication Data

US 2010/0241115 A1 Sep. 23, 2010

Related U.S. Application Data

(60) Provisional application No. 61/210,311, filed on Mar. 17, 2009.

(51) Int. Cl.
*A61B 18/14* (2006.01)

(52) U.S. Cl.
USPC ......... 606/38; 606/1; 606/33; 606/34; 606/50

(58) Field of Classification Search
USPC .................. 606/33, 34, 38–42, 45, 48–50, 1
See application file for complete search history.

(56) References Cited

U.S. PATENT DOCUMENTS

| | | | |
|---|---|---|---|
| 4,658,819 A | 4/1987 | Harris et al. | |
| 5,039,973 A * | 8/1991 | Carballo | 338/153 |
| 5,514,129 A | 5/1996 | Smith | |
| 5,871,469 A | 2/1999 | Eggers et al. | |
| 6,264,650 B1 * | 7/2001 | Hovda et al. | 606/32 |
| 6,436,097 B1 | 8/2002 | Nardella | |
| 6,652,514 B2 | 11/2003 | Ellman et al. | |
| 6,712,813 B2 | 3/2004 | Ellman et al. | |
| 6,994,707 B2 | 2/2006 | Ellman et al. | |
| 7,195,627 B2 | 3/2007 | Amoah et al. | |
| 7,211,081 B2 | 5/2007 | Goble | |
| 7,883,458 B2 * | 2/2011 | Hamel | 600/1 |
| 2001/0049524 A1 * | 12/2001 | Morgan et al. | 606/50 |
| 2002/0087179 A1 * | 7/2002 | Culp et al. | 606/167 |
| 2002/0115917 A1 * | 8/2002 | Honda et al. | 600/301 |
| 2002/0156466 A1 * | 10/2002 | Sakurai et al. | 606/1 |
| 2003/0050633 A1 * | 3/2003 | Ellman et al. | 606/37 |
| 2005/0075545 A1 * | 4/2005 | Honda et al. | 600/301 |
| 2005/0251228 A1 * | 11/2005 | Hamel | 607/60 |
| 2006/0116667 A1 * | 6/2006 | Hamel et al. | 606/1 |
| 2006/0217700 A1 * | 9/2006 | Garito et al. | 606/34 |
| 2007/0129726 A1 | 6/2007 | Eder et al. | |
| 2007/0167941 A1 | 7/2007 | Hamel et al. | |
| 2007/0167942 A1 | 7/2007 | Rick | |
| 2008/0039831 A1 | 2/2008 | Odom et al. | |
| 2010/0268211 A1 * | 10/2010 | Manwaring et al. | 606/30 |

* cited by examiner

*Primary Examiner* — Michael Peffley
*Assistant Examiner* — Khadijeh Vahdat
(74) *Attorney, Agent, or Firm* — Flynn, Thiel, Boutell & Tanis, P.C.

(57) ABSTRACT

An electrosurgical system is capable of selectively varying the power applied to an electrosurgical probe, without interruption or discontinuity, in a variable mode or providing a constant coagulation power value to the probe. In a fixed mode, power to the electrosurgical probe must be discontinued to change the power level output by the probe. A single controller is capable of operating the probe in the variable mode and the fixed mode. The controller includes an actuator for stopping the cutting operation and then switching to a constant coagulation output during either of the variable mode or the fixed mode. The controller of the system may selectively control a separate surgical tool.

17 Claims, 12 Drawing Sheets ial Application Ser. No. 61/210,311, filed Mar. 17, 2009, which is incorporated herein by reference in its entirety.
METHOD AND SYSTEM FOR VARYING OUTPUT INTENSITY OF ENERGY APPLIED TO AN ELECTROSURGICAL PROBE

CROSS REFERENCE TO RELATED APPLICATION

This application claims the benefit of U.S. Provisional Application Ser. No. 61/210,311, filed Mar. 17, 2009, which is incorporated herein by reference in its entirety.

FIELD OF THE INVENTION

This invention is related generally to an electrosurgical system having a controller for selectively changing the intensity of power applied to an electrosurgical probe in a cutting mode and providing a constant power to the probe in a coagulation mode. The system can include a mechanically powered tool that shares a control console with the electrosurgical probe.

BACKGROUND OF THE INVENTION

Endoscopy in the medical field allows internal features of the body of a patient to be viewed without the use of traditional, fully-invasive surgery. Endoscopic imaging systems enable a user to view a surgical site and endoscopic cutting tools enable non-invasive surgery at the site. For instance, an RF generator provides energy to a distal end tip of an RF probe within the surgical site. In one mode, the RF probe provides RF energy at a power level to ablate or otherwise surgically remove tissue. In another instance, RF energy is provided to the RF probe in order to coagulate the tissue at the surgical site to minimize bleeding thereat.

Tissue ablation is achieved when a high power electrical signal having a sufficiently large voltage is generated by a control console and directed to an attached probe. Application of the high power signal to the probe results in a large voltage difference between the two electrodes located at the tip of the probe (presuming a bipolar probe), with the active electrode being generally 200 volts more than the passive or return electrode. This large voltage difference leads to the formation of an ionized region between the two electrodes, establishing a high energy field at the tip of the probe. Applying the tip of the probe to organic tissue leads to a rapid rise in the internal temperature of the cells making up the neighboring tissue. This rapid rise in temperature near instantaneously causes the intracellular water to boil and the cells to burst and vaporize, a process otherwise known as tissue ablation. An electrosurgical "cut" is thus made by the path of disrupted cells that are ablated by the extremely hot, high energy ionized region maintained at the tip of the probe. An added benefit of electrosurgical cuts is that they cause relatively little bleeding, which is the result of dissipation of heat to the tissue at the margins of the cut that produces a zone of coagulation along the cut edge.

In contrast to tissue ablation, the application of a low power electrical signal having a relatively low voltage to the active electrode located at the tip of the probe results in coagulation. Specifically, the lower voltage difference established between the active and return electrodes results in a relatively slow heating of the cells, which in turn causes desiccation or dehydration of the tissue without causing the cells to burst.

FIG. 1 corresponds to FIG. 1 of U.S. Patent Publication No. 2007/0167941, owned by the same assignee hereof, the disclosure of which is hereby incorporated by reference.

As illustrated in FIG. 1, a typical electrosurgical system 10 includes an electrosurgical probe 12 (hereafter referred to simply as "probe") and a control console or controller 14. Interface 15 enables configuration of various devices connected to the console 14. The probe 12 generally comprises an elongated shaft 16 with a handle or body 18 at one end and a tip 20 at the opposite end. A single active electrode 19 is provided at the tip 20 if the probe 12 is of a "monopolar" design. Conversely, the probe 12 may be provided with both an active electrode 19 and a return electrode 21 at the tip 20 if the probe is "bipolar" in design. The probe 12 connects to control console 14 by means of a detachable cable 22. The current for energizing the probe 12 comes from control console 14. When actuated, the control console 14 generates a power signal suitable for applying across the electrode(s) located at the tip 20 of the probe 12. Specifically, current generated by the control console 14 travels through the cable 22 and down the shaft 16 to tip 20, where the current subsequently energizes the active electrode 19. If the probe 12 is monopolar, the current will depart from tip 20 and travel through the patient's body to a remote return electrode, such as a grounding pad. If the probe 12 is bipolar, the current will primarily pass from the active electrode 19 located at tip 20 to the return electrode 21, also located at tip 20, and subsequently along a return path back up the shaft 16 and through the detachable cable 22 to the control console 14.

After configuration of the control console 14 is carried out by means of the interface 15, actuation and control of the probe 12 by the surgeon is accomplished by one or more switches 23, typically located on the probe 12. One or more remote controllers, such as, for example, a footswitch 24 having additional switches 25-28, respectively, may also be utilized to provide the surgeon with greater control over the system 10. In response to the surgeon's manipulation of the various switches 23 on the probe 12 and/or remote footswitch 24, the control console 14 generates and applies various low and high power signals to electrode 19.

Actuation of coagulation switch 26 of footswitch 24 results in coagulation of the tissue adjacent the tip 20 of the probe 12. While operating in coagulation mode, the control console 14 of the prior art system shown in FIG. 1 is configured to drive the electrosurgical probe at a low, but constant, power level. Due to inherent varying conditions in tissue (i.e., the presence of connective tissue versus fatty tissue, as well as the presence or absence of saline solution), the impedance or load that the system experiences may vary. According to Ohm's law, a change in impedance will result in a change in current levels and/or a change in voltage levels, which in turn, will result in changing power levels. If the operating power level of the system changes by more than a predefined amount, the control console 14 will attempt to compensate and return the power back to its originally designated level by regulating either the voltage and/or current of the power signal being generated by the console and used to drive the attached probe 12.

Electrosurgical systems 10 also have a cutting mode for cutting tissue. Actuation of cutting switch 25 of the footswitch 24 places the electrosurgical system 10 in the cutting or ablation mode by application of a high energy signal to probe 12. In the cutting mode, the controller 14 outputs constant energy to the electrosurgical probe 12 while an operator maintains at least a predetermined force to actuate the cutting switch 25.

In a cutting operation, to change the power level of energy applied to the electrosurgical probe 12, the cutting switch 25 must be off. Then a user actuates either of switches 27, 28 on the footswitch 24, which function as controls for increasing and decreasing the power intensity output level, respectively. The electrosurgical system 10 senses actuation of increase switch 27 for increasing the power intensity value for output by the control console 14 depending on the original intensity value setting and the number of times the switch 27 is pressed. Likewise the electrosurgical system senses actuation of decrease switch 28 for decreasing the power intensity value from a previous value. Then, upon actuation of switch 25, the RF generator in the console 14 applies power to the probe 12 at the newly selected power level.

While the system shown in FIG. 1 adjusts cutting energy that is output from an RF generator in the control console 14, the changes in power level are made while the RF generator is off. Thus, a cutting operation must be interrupted or discontinued to change the power level. FIG. 2 shows one example wherein eleven separate discrete power levels are selectable for an electrosurgical system. Turning off energy to the electrode 19 to change power levels increases the length of time required to perform a surgery, which can be detrimental to the patient.

In the electrosurgical system 10 shown in FIG. 1, a non-volatile memory device (not shown) and reader/writer (not shown) can be incorporated into the handle 18 of the electrosurgical probe 12, or alternatively, incorporated into or on the cable 22 that is part of the probe 12 and which is used to connect the probe 12 to the control console 14 of the system. Alternatively, the memory device may be configured so as to be incorporated into or on the communication port that is located at the free end of the cable 22 and which is used to interface the cable with a corresponding port on the control console 14.

During manufacturing of the probe shown in FIG. 1, data representing probe-specific operating parameters is loaded into the memory device. Upon connection of the probe 12 to the control console 14 of the electrosurgical system 10, the data stored in the probe's non-volatile memory can be accessed by a reader and forwarded on to the control console 14. As such, once an electrosurgical probe 12 is connected, the control console 14 accesses the configuration data of the specific probe 12 and automatically configures itself based on the operating parameters of the probe.

Beyond probe-specific operating parameters, the memory device within each attachable probe 12 can store additional data concerning usage of the probe. This usage data includes a variety of information. For example, usage data may represent the number of times an electrosurgical probe 12 has been used, or the duration of the time that the probe has been activated overall or operated at different power levels. Additional usage data may restrict the amount of time that a specific attachable probe can be used. In addition to usage data, the prior art memory device can store information concerning any errors that were encountered during use of the probe 12.

One embodiment of the invention is directed to a system for an electrosurgical probe that dynamically adjusts power output from the probe without deactivating and then reactivating an RF generator. This arrangement can minimize the length of time for an operating procedure.

One embodiment of the invention disclosed herein is directed to improving cutting of tissue by an electrosurgical probe, such as by manually adjusting or varying the intensity of power delivered to tissue by a generator without temporarily interrupting the application of power. This arrangement also includes an actuator for coagulating tissue at a constant power level.

In another embodiment of the invention, operation of an electrosurgical system is obtained by providing a controller to vary the intensity of power applied to an electrosurgical probe without disruption in a first variable mode, and by providing a second fixed mode wherein energy to the RF probe is discontinued to allow a user to change the power level.

DETAILED DESCRIPTION

Figure 3:
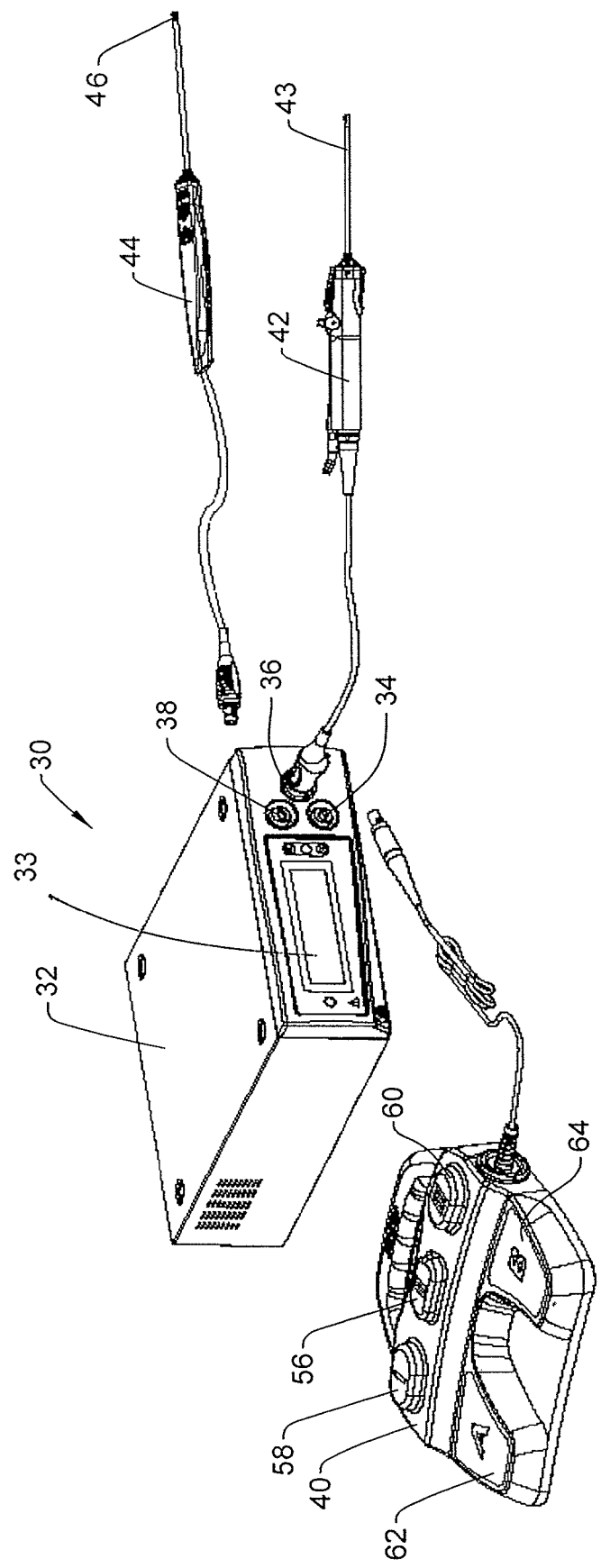
FIG. 3 depicts an electrosurgical system of the invention that includes a foot controller, an electrosurgical probe and a powered surgical handpiece for attachment to a control console.

FIG. 3 shows a surgical system 30 including a console 32 having a visual display screen 33, a footswitch receiving port 34, a handpiece receiving port 36, an RF probe receiving port 38 and control console selectors. The visual display screen 33 displays devices connected to the receiving ports 36, 38. The display screen 33 is capable of displaying a plurality of modes for selection in response to actuation of selected ones of the console selectors. The footswitch receiving port 34 provides a connection to the control console 32 for a foot controller 40. Handpiece receiving port 36 receives the connection jack of a powered surgical handpiece 42 with a cutting element attached thereto, for instance a mechanical cutting tool or cutting element 43, such as a burr. The powered surgical handpiece 42 can control oscillation or rotation speed of the mechanical cutting tool 43 secured thereto in response to actuation of the foot controller 40. RF probe receiving port 38 receives a connecting jack of an RF or electrosurgical probe 44 having an electrode 46. In some embodiments, control console selectors include push buttons that control or scroll through menus shown on the visual display screen 33 of the control console 32. In some instances, one or more of the selectors select user preferences for particular operating modes of the surgical handpiece 42 with a mechanical cutting element 43, such as a burr secured thereto or the electrosurgical probe 44 of the surgical system 30.

The handpiece 42 of the surgical system 30 includes a transceiver (not shown) and a non-volatile memory device (not shown). The transceiver acts as a reading device for reading cutter-specific data from the cutting element 43.

Figure 4:
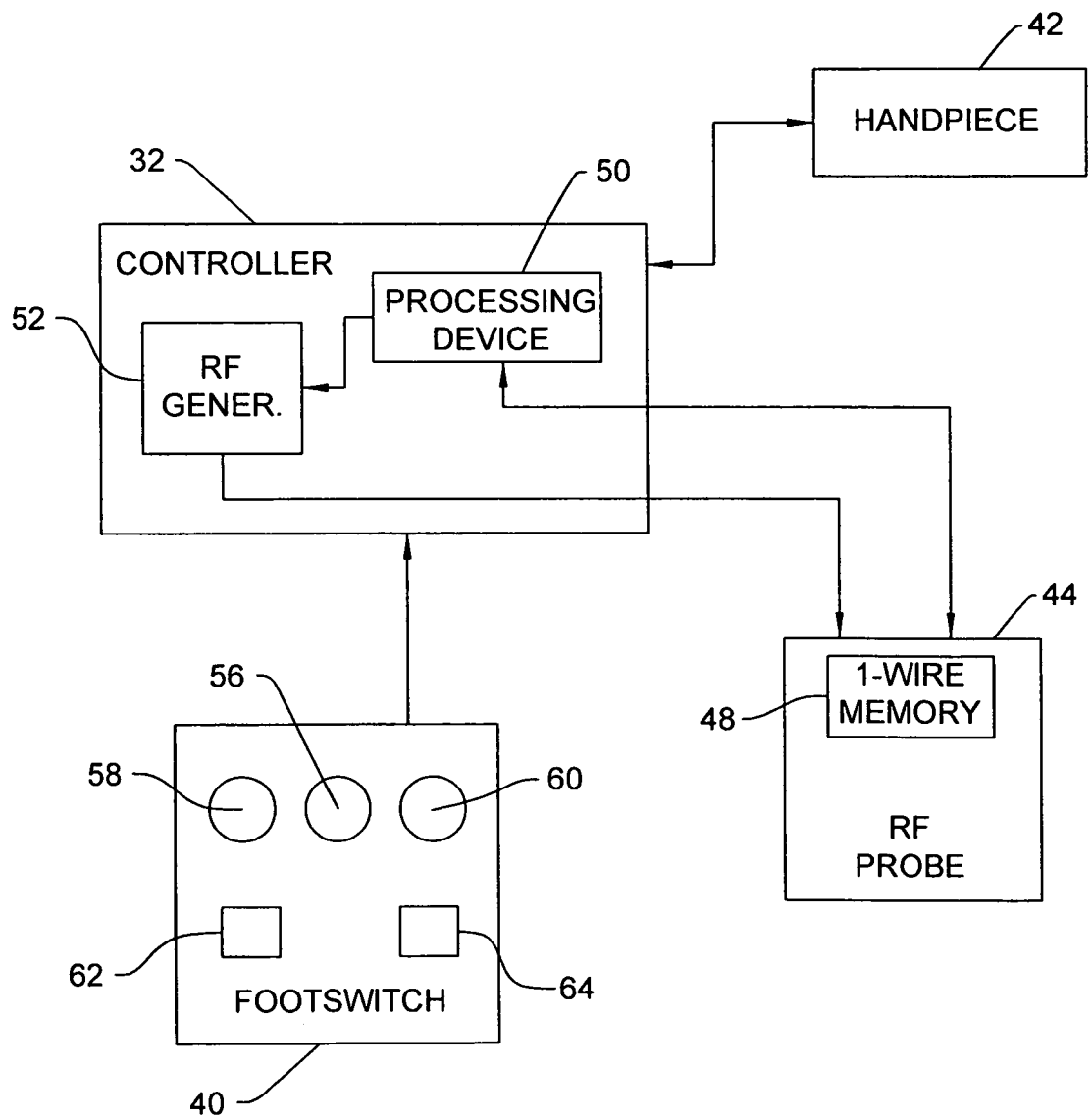
FIG. 4 is a block diagram of the electrosurgical system.

One embodiment of the RF probe structure generally corresponds to the probe structure illustrated in FIG. 1, except additional probe-specific data, described later herein, is provided on a one-wire memory 48 as shown in FIG. 4 for reading by the control console 32. The control console 32 includes a processing device 50 for processing the data received from the one-wire memory device 48. The processing device 50 shown in FIG. 4 controls an RF generator 52 that provides RF energy to the electrosurgical probe 44 to power the electrode 46 disposed at the distal end thereof.

Controller

Figure 5:
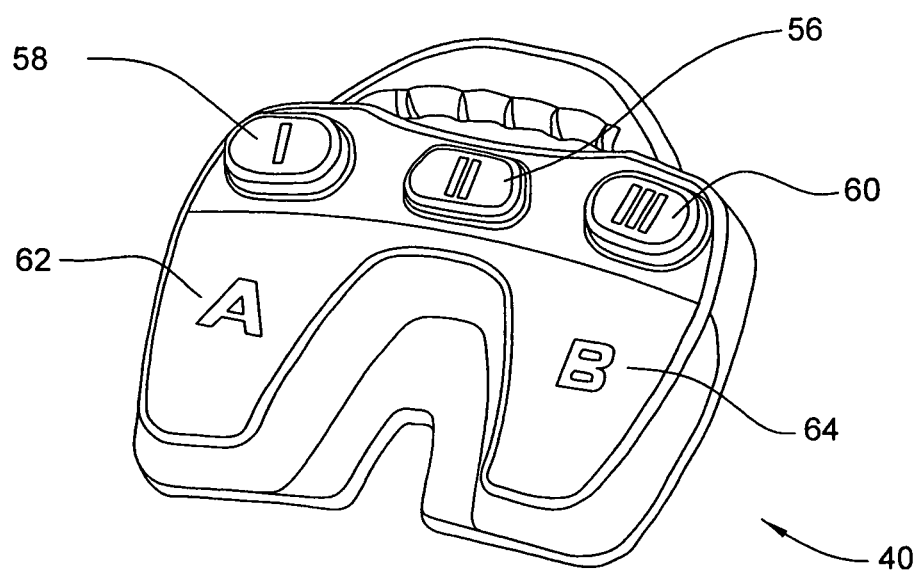
FIG. 5 is a top perspective view of the foot controller shown in FIG. 3.

The foot controller 40 illustrated in FIGS. 3-5 is similar in structure to the remote console disclosed in U.S. Patent Publication No. 2006/0116667, owned by the same assignee hereof, the disclosure of which is hereby incorporated by reference.

As shown in FIG. 5, the foot controller 40 includes a device selection actuator 56, a power decrease actuator 58 and a power increase actuator 60. The device selection actuator 56 chooses between a powered surgical handpiece 42 and an electrosurgical probe 44 that are connected to the control console 32 for operation thereof. Further, the controller 40 includes a cutting power actuator 62 and a coagulation actuator 64 for operating the electrosurgical probe 44 when the probe is selected. In the fixed cutting mode, the actuator 62 acts as a switch that enables cutting by the electrosurgical probe 44. In the variable cutting mode, the actuator 62 provides a changing output value depending on the total force applied thereto. Detailed operation of the foot controller 40 for the surgical system 30 is discussed below.

Electrosurgical Probe Routine

Figure 6:
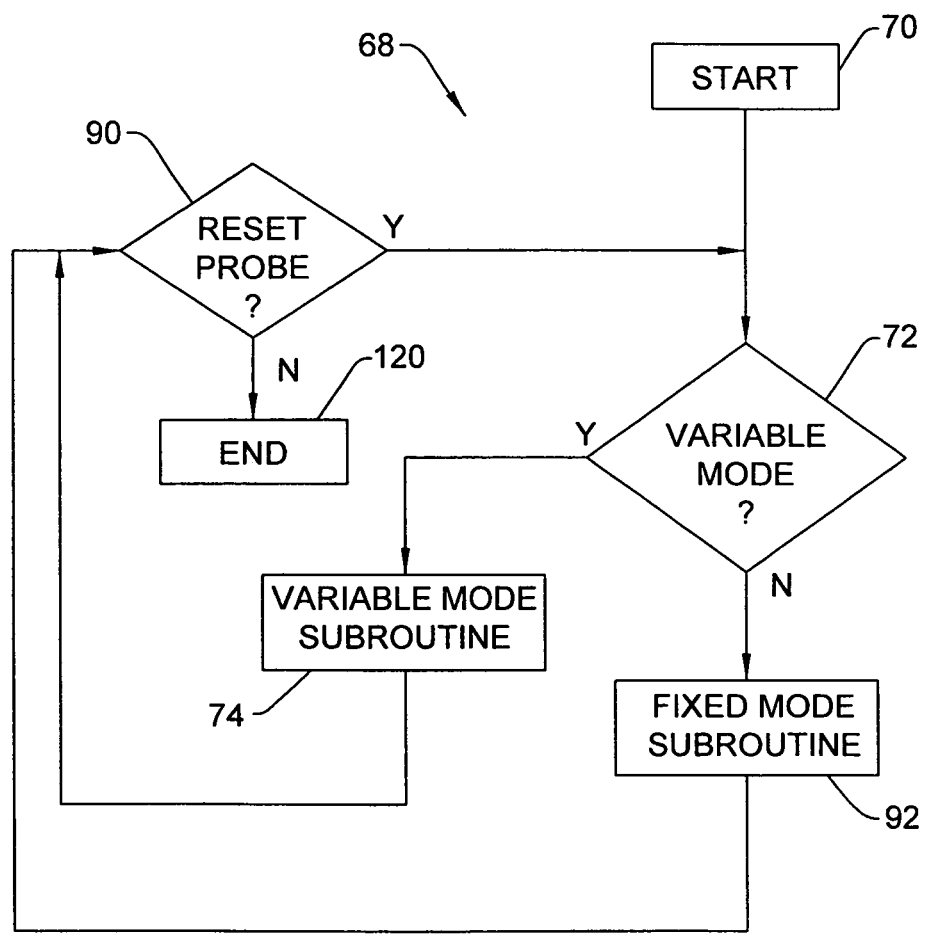
FIG. 6 is a flow chart showing steps for controlling power to an electrosurgical probe depending on selected operating modes.

FIG. 6 is a flow chart representing an electrosurgical probe routine 68 for a processing device 50 operating the RF generator 52 that supplies power to the electrosurgical probe 44. In one embodiment of the invention, selectors of the control console 32 enable an operator to select between a variable mode and a fixed mode for operation of the electrosurgical probe 44.

The probe routine 68 illustrated in FIG. 6 begins at start 70. A user selects the variable mode or the fixed mode. Further, other modes for selection, such as a device configuration mode are contemplated. In another embodiment, a user selects a menu entry that initializes settings of the surgical system 30 using the stored preference information for a particular user. In other embodiments, a selection switch is provided to select the operating mode.

At step 72, the processing device 50 determines if the variable mode or the fixed mode has been selected. If the variable mode is chosen by a user, the processing device advances to step 74.

Variable Mode Subroutine

Figure 7:
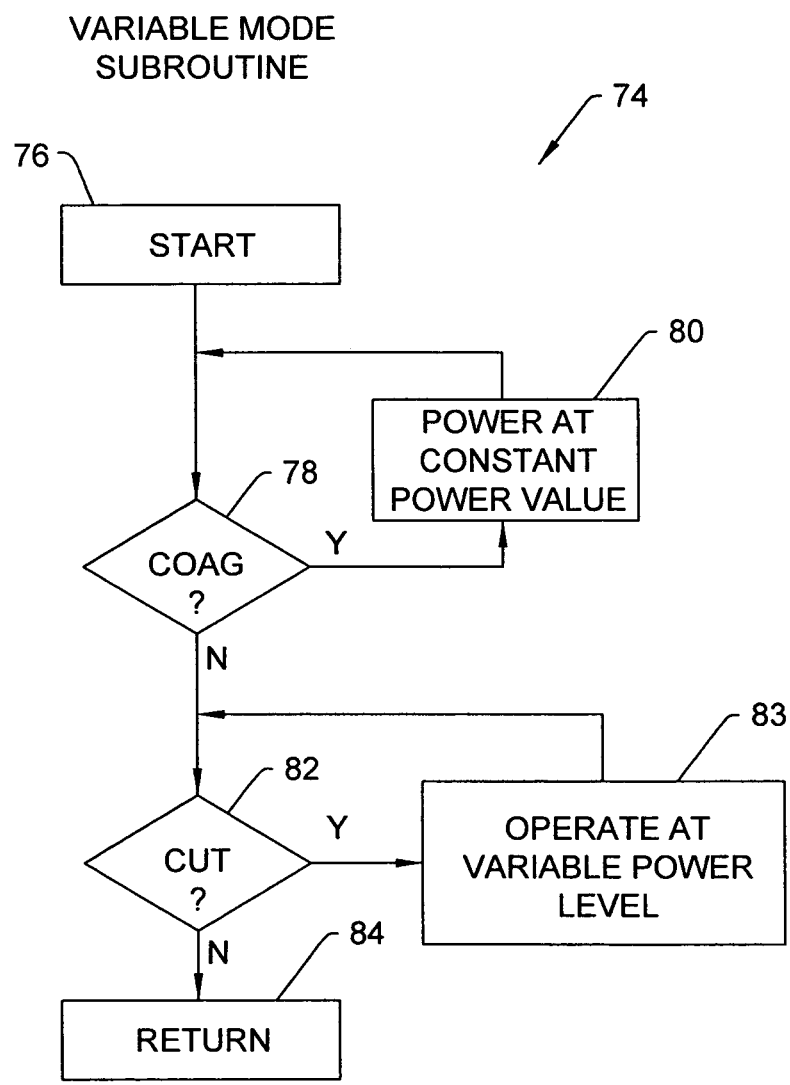
FIG. 7 is a flow chart for a variable mode subroutine that provides varying power levels to an electrosurgical probe without discontinuing power to the probe.

When variable mode subroutine 74 is selected, the processing device 50 executes the variable subroutine illustrated in FIG. 7. From start 76, the variable mode subroutine 74 advances to coagulation decision step 78. If the coagulation actuator 64 provides a coagulation signal, the processing device 50 advances to step 80 and outputs a constant predetermined power value from the RF generator 52. The RF generator 52 provides the constant predetermined coagulation power value to the electrosurgical probe 44 to coagulate tissue. The processing device 50 then returns to decision step 78 and determines if the coagulation actuator 64 continues to be pressed.

In the instance when the coagulation actuator 64 is not depressed, the variable mode subroutine 74 of the processing device 50 advances to step 82. At step 82, the processing device 50 determines whether the dual purpose power actuator 62 is depressed, and if depressed, a measured force or control value from the dual purpose power actuator 62 is provided to the processing device 50. At step 83, depending on the amount of force applied to the actuator 62, such as a foot pedal, the processing device 50 controls the RF generator 52 to output a discrete power level from the electrosurgical probe 44 that is proportional with respect to the measured force or sensed control value received from the actuator 62. So long as the actuator 62 is depressed, at decision step 82 the routine advances to execute at step 83 and then returns to step 82 of the variable mode subroutine 74 and repeats same. When the actuator 62 is not depressed at decision step 82, the variable mode subroutine 74 advances to return 84 and the variable mode subroutine ends.

Figure 8:
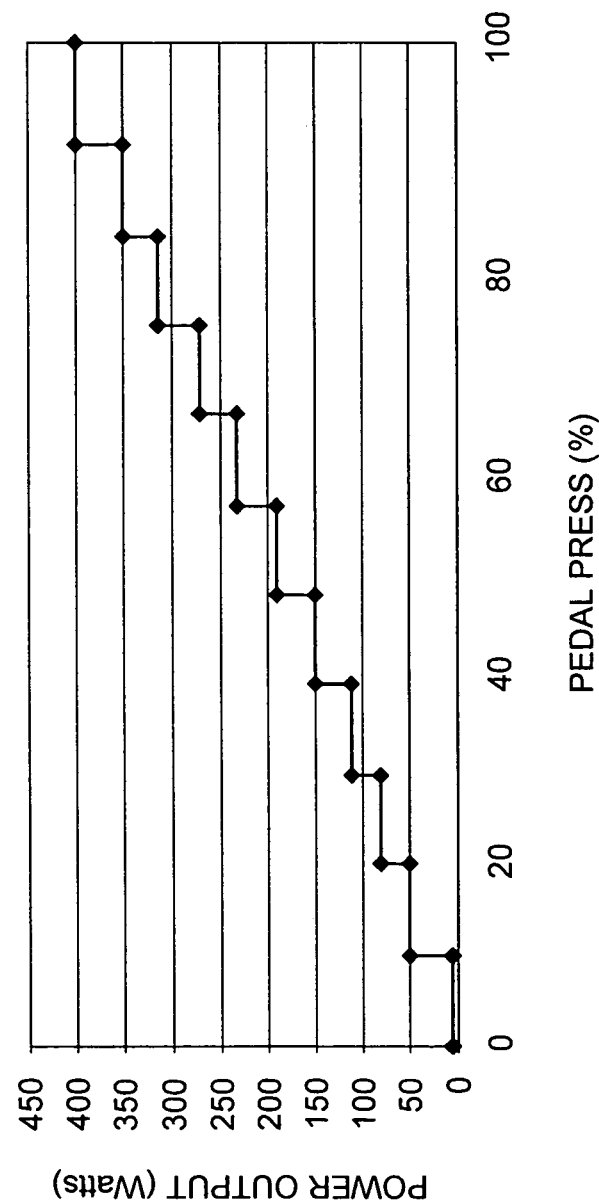
FIG. 8 illustrates a graph showing delivered power versus percentage of pedal press of an actuator.

The variable mode enables an operator to select from the various power level outputs illustrated in FIG. 8 while being capable of providing different power levels to the electrosurgical probe 44 without first discontinuing power to the probe. The pedal press or force applied to the actuator 62 provides essentially instantaneous variable power control of the power output from the RF generator 52. As shown in the embodiment of FIG. 8, the percentage of applied pedal force/pressure or pedal travel extends from 0% to 100% and corresponds to eleven different discrete power levels or values that depend on the force applied to the actuator 62. In another embodiment, the amount of movement of a pedal of the actuator 62 controls the power level provided by the RF generator 52.

Returning to FIG. 6, when the power actuator 62 no longer receives at least a predetermined force, the processing device 50 advances to probe reset decision step 90. At step 90, the processing device 50 determines if a selector of the control console 32 has been operated to select the other electrosurgical probe operating mode, a configuration routine or other operating mode for execution by processing device 50. If one of the electrosurgical probe mode subroutines 74, 92 is or remains selected, the processing device 50 advances to step 72.

In one embodiment, the actuator 62 includes a hall effect sensor that determines the movement or position of a pedal of the actuator and controls the power levels as illustrated in FIG. 8. Further, in some embodiments the actuator 62 is a force transducer or pressure transducer for sensing force applied thereto, without necessarily having significant movement of a foot pedal or other element thereof. In these embodiments the power level output can be linear with respect to the force applied to the pedal of the actuator 62. In other embodiments the power level output is non-linear with respect to the force applied to the pedal.

In some embodiments the actuator 62 is a position sensor including a series of position responsive switches actuated in response to the amount of movement of a pedal of the actuator to provide a linear increase in the power level with respect to movement of the pedal. In some embodiments the power level output is non-linear with respect to foot travel distance or movement of the actuator 62.

While FIG. 8 shows eleven discrete power levels for the variable mode of operation, fewer or more power levels can be provided. For example, in some embodiments twenty or more power levels are correlated with the force applied to the actuator 62 and provided to processing device 50 to obtain a more precise output power level control. As discussed above, the variable mode results in less cutting delay and thus a less time consuming surgical procedure.

In some embodiments, a default to the variable mode or to the fixed mode for the electrosurgical probe 44 is provided when the surgical system 30 is initially powered on.

Fixed Mode Subroutine

Figure 9:
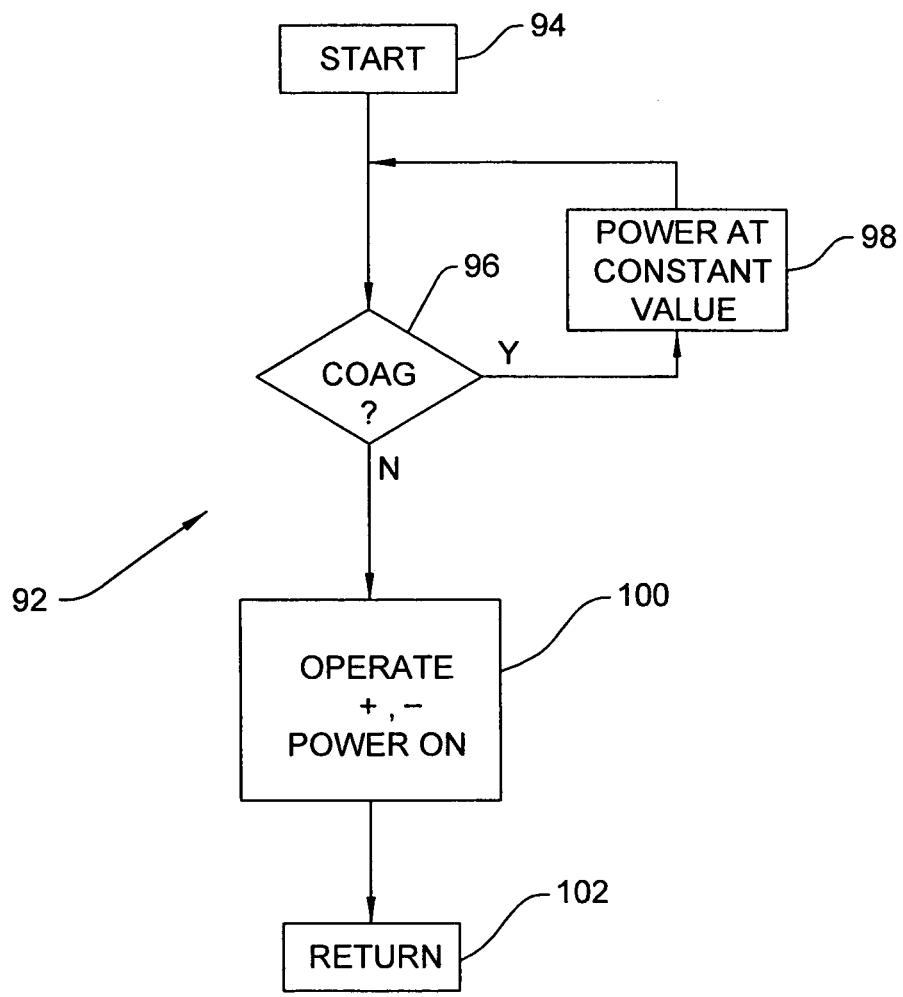
FIG. 9 is a flow chart for a fixed mode subroutine that requires no application of power to an electrosurgical probe to change a power level value.

At decision step 72 in probe routine 68 shown in FIG. 6, if the variable mode is not indicated at decision step 72, the processing device 50 advances to fixed mode subroutine 92 shown in FIG. 9.

The fixed mode subroutine 92 shown in FIG. 9 executes by advancing from start 94 to coagulation decision step 96. In the fixed mode subroutine 92, if the coagulation actuator 64 is depressed, the processing device 50 advances to step 98. At step 98, the processing device 50 operates to provide an essentially constant coagulation power value from the RF generator 52 to the electrosurgical probe 44. As shown in FIG. 9, from step 98, the processing device 50 returns to coagulation decision step 96. At step 96, if the coagulation actuator 64 is not actuated, the coagulation power value is no longer output and the processing device 50 advances to step 100.

At step 100, the processing device determines if any of actuators 58, 60 and 62 are depressed. If actuator 62 is depressed, the RF generator 52 provides power to the electrosurgical probe 44 at an initial power value or level provided at system start-up or at a power level previously set by a user operating the control console 32. If the actuator 62 is depressed to enable power to the electrosurgical probe 44, actuators 58, 60 are disabled and do not function. Thus the power level provided by the RF generator 52 to the electrosurgical probe 44 remains essentially constant.

Figure 2:
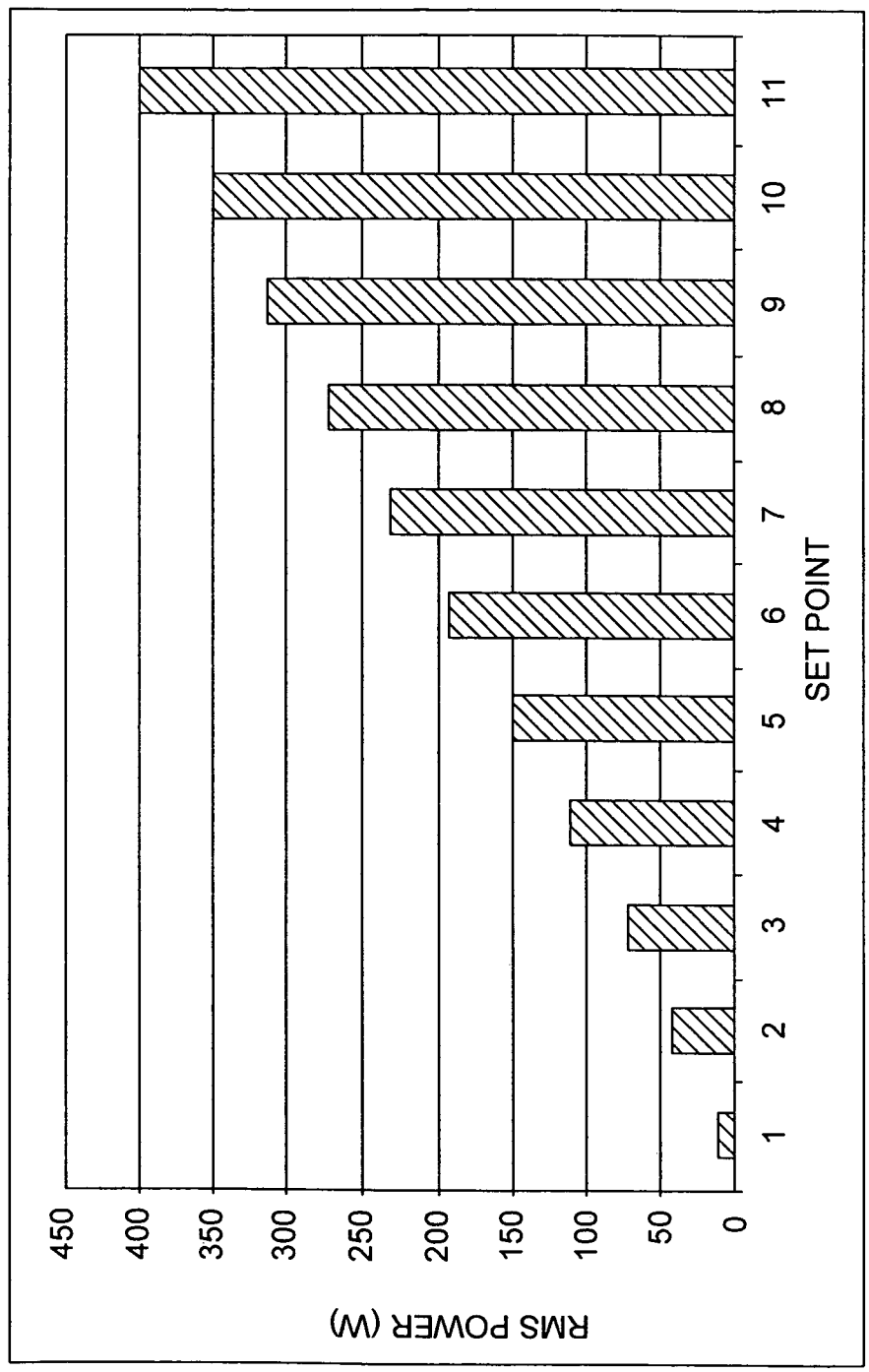
FIG. 2 is a graph showing output power at a plurality of set points having corresponding different power levels.

At step 100, if power increase actuator 60 is depressed with actuator 62 not operative, the discrete power level to be output by the RF generator 52 is increased. In some embodiments, the power level increases in a manner corresponding to the various set points for discrete power level as shown in FIG. 2, for each actuation of actuator 60 that is sensed by foot controller 40 and provided to the processor device 50.

If the power decrease actuator 58 is operated at step 100 with actuator 62 not operative, the discrete power level value is decreased for each actuation thereof. The power level decreases in a manner generally corresponding to the various set points for discrete power level as illustrated, for example, in FIG. 2 for each actuation of the actuator 58. At return step 102, the fixed mode subroutine 92 returns to the electrosurgical probe routine 68 shown in FIG. 6.

Tool/Probe Routine

Figure 10:
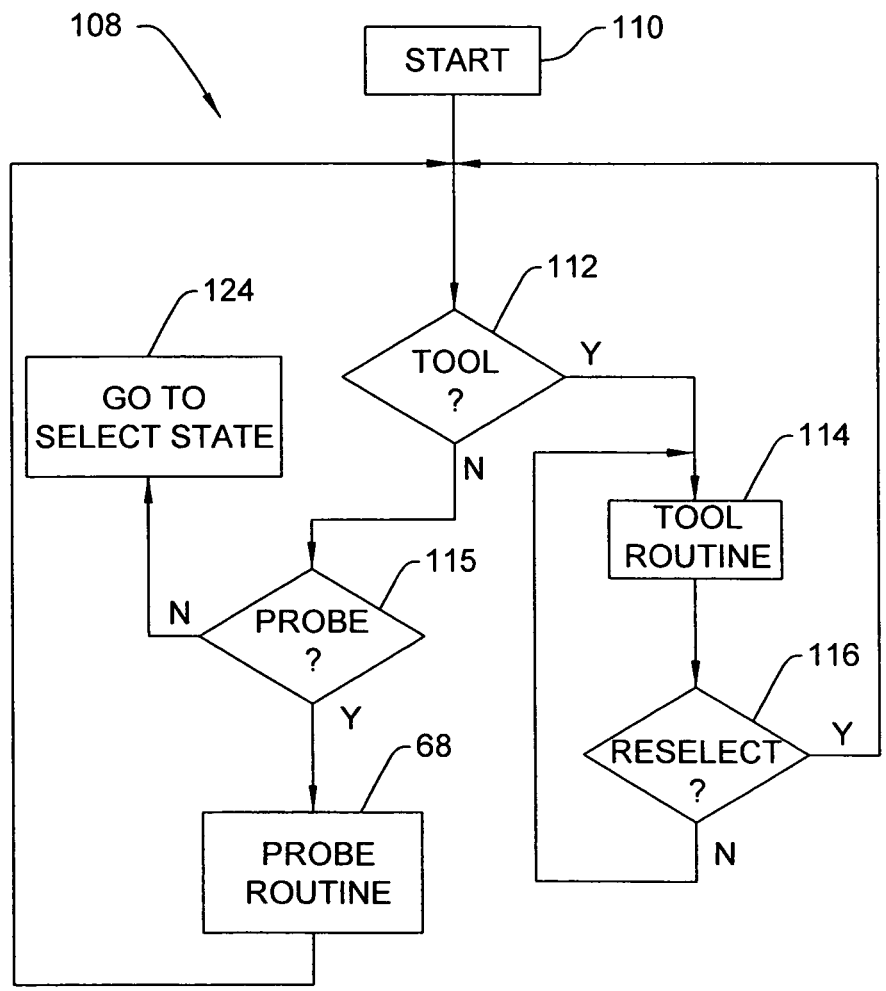
FIG. 10 is a tool/probe routine which includes selecting the device to be operated.

FIG. 10 is a flow chart directed to a tool/probe routine 108 for the processing device 50. The routine 108 begins at start 110 and advances to a tool decision step 112. When tool operation is selected at decision step 112, the processing device 50 advances to tool routine 114. Tool routine 114 is a known method of operating the cutting element 43 mounted to the powered surgical handpiece 42. U.S. Patent Publication No. 2006/0116667 discloses an arrangement wherein various elements are operated with one controller. Thus, the tool routine 114 will not be discussed in detail herein.

In tool routine 114, the actuators on the foot controller 40 control the powered surgical handpiece 42 to power a cutting element 43 to cut tissue. After tool routine 114, operation of the processing device 50 advances to decision step 116. At step 116, if a different device or mode is not selected, the processing device 50 returns to tool routine 114 and continues to operate the mechanical cutting tool or cutting element 43 that is mounted to the powered handpiece 42.

When a device reselection has been determined at step 116, the processing device 50 returns to tool decision step 112. At tool decision step 112, if the tool is not selected, the processing device 50 advances to probe decision step 115. If an electrosurgical probe operation is selected by the actuator 56, the processing device 50 advances to electrosurgical probe routine 68 illustrated in FIG. 6. The probe routine 68 operates as discussed above until electrosurgical probe operation is discontinued as illustrated at step 120 in FIG. 6 and can eventually return to the tool decision step 112 illustrated in FIG. 10.

In FIG. 10, if the electrosurgical probe is not selected at decision step 115, the processing device 50 can advance to select state 124.

The term "select state" references a state wherein a large number of additional modes can be operated, such as configuration modes or the like.

Figure 1:
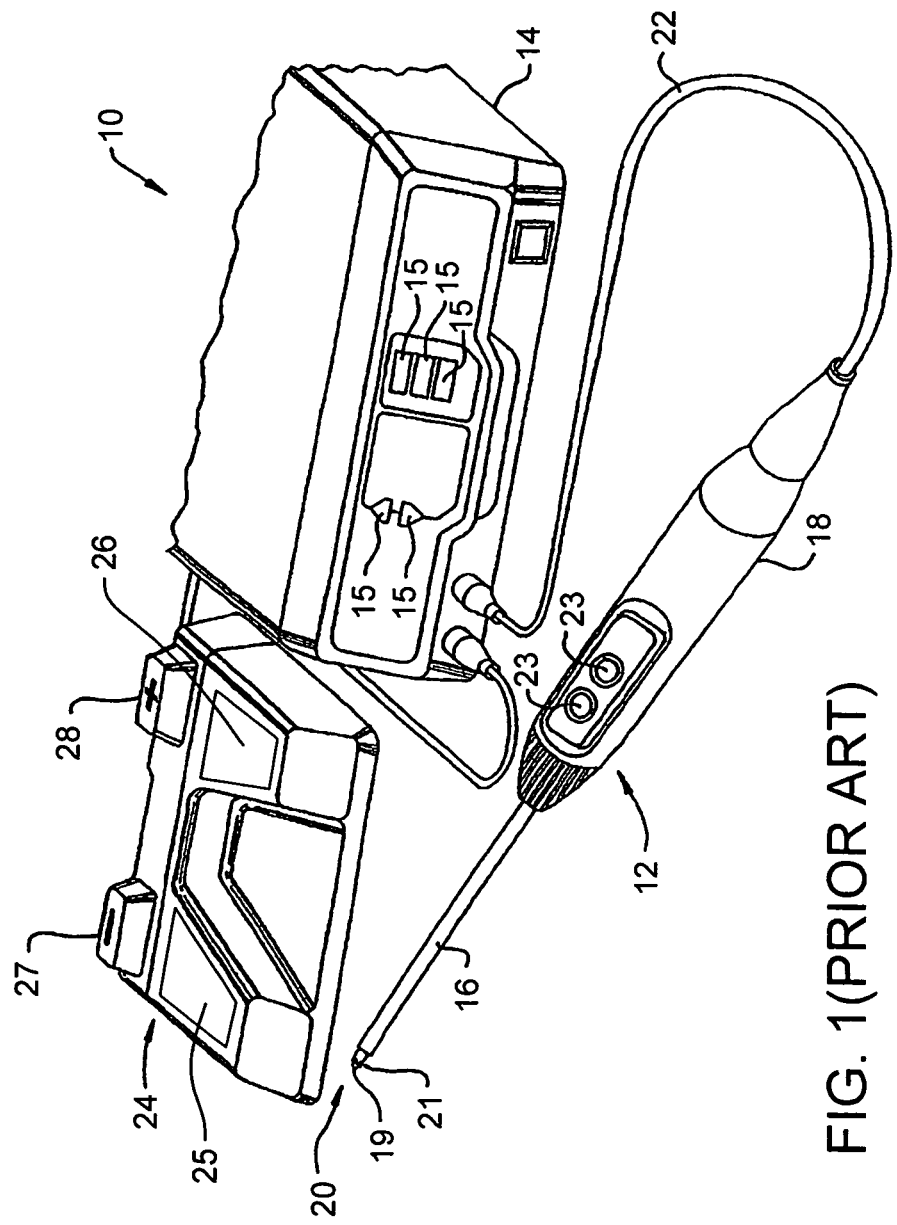
FIG. 1 depicts an electrosurgical system that includes an electrosurgical probe connected to a control console, along with a footswitch.

One mode, as discussed in FIG. 1, includes reading of one-wire memory devices 48 or reading of RFID chips disposed in the electrosurgical probe 44 or in the powered surgical handpiece 42. Such data is received by the processing device 50 and stored therein to assist in operation thereof. For instance, data related to the operating parameters of the cutting element 43 mounted to the powered surgical handpiece 42, or related to the electrosurgical probe 44 having an electrode 46, may be stored by the processing device 50 to ensure proper operation thereof.

In other embodiments, additional operating modes or subroutines enable control of both the cutting element 43 and electrode 46 simultaneously with actuators on at least one of the handpiece 42, the electrosurgical probe 44 and the control console 32, along with the controller 40.

Alternative Electrosurgical Probe Routine

Figure 11:
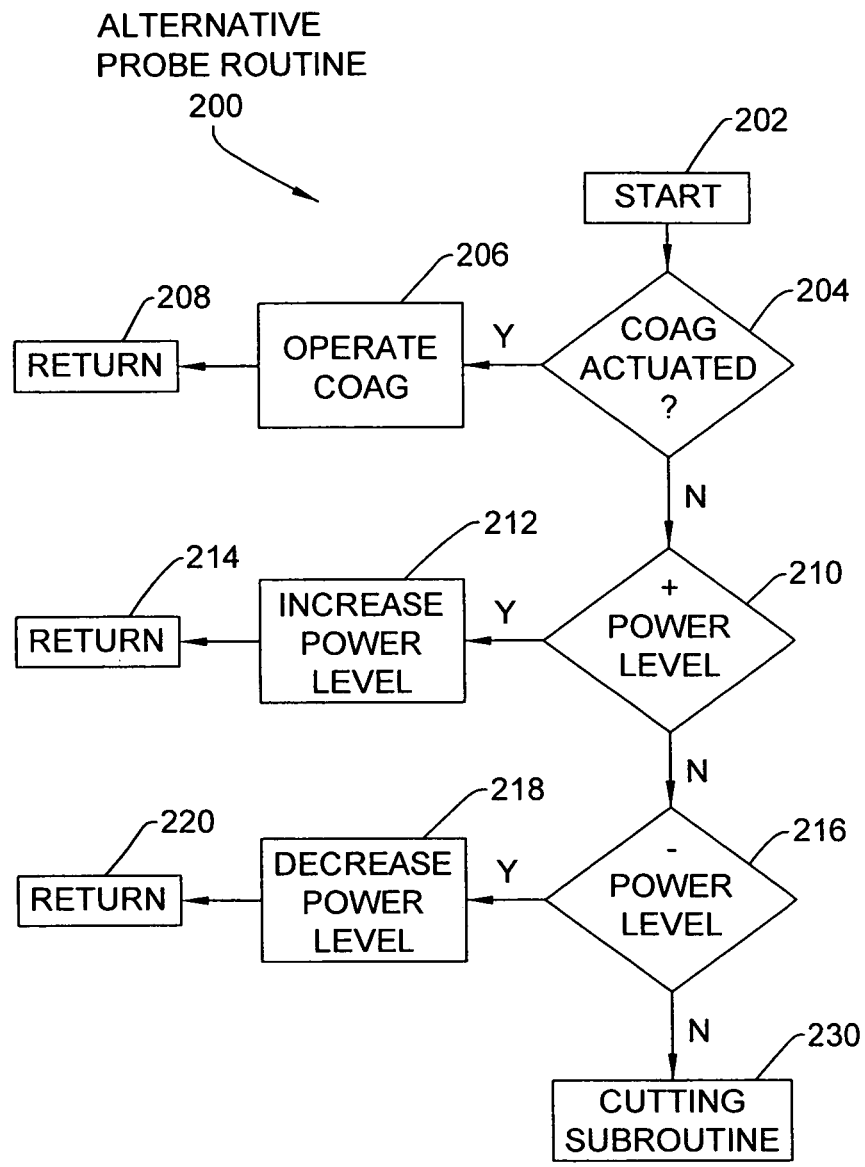
FIG. 11 is a flow chart showing a second embodiment for controlling an electrosurgical probe.

FIG. 11 is a flow chart representing a second embodiment of an electrosurgical probe routine. The electrosurgical probe routine 200 shown in FIG. 11 is executed by processing device 50 to control the RF generator 52 that supplies power to the electrosurgical probe 44. The electrosurgical probe routine 200 begins at start 202. In one embodiment, at start 202 the processing device 50 already has stored therein available default preferences for a particular user with regard to pre-selection of the variable or fixed operating mode and properties of the particular electrosurgical probe 44 connected to the console.

From start 202, the routine 200 advances to coagulation decision step 204. The processor 50 determines if the coagulation actuator 64 is enabled. If so, the processor 50 advances to step 206. At step 206, the processor 50 controls the RF generator 52 to supply coagulation power to the electrosurgical probe 44 so long as the actuator 64 is enabled. When the actuator 64 is disengaged, the processor 50 advances to return step 208 and returns to start 202.

Returning to coagulation decision step 204, when the processor 50 determines that the coagulation actuator 64 is not enabled, the probe routine 200 advances to increase power level decision step 210. At decision step 210, the processor 50 determines if the power increase actuator 60 is enabled. When the power increase actuator 60 is enabled, the routine 200 advances to step 212. At step 212, the stored power level value for the cutting operation is increased or incremented by a discrete power level value.

In some embodiments, if the discrete power level is at a maximum value and thus cannot be further increased, enabling of the power increase actuator 60 selects the fixed cutting mode for operation instead of the variable cutting mode or maintains the fixed cutting mode. In other embodiments, the processor 50 changes the electrosurgical probe arrangement from the fixed cutting mode to the variable cutting mode, or remains in the variable cutting mode, when the power increase actuator 60 is enabled while at the maximum power level value.

After the power increase actuator 60 is disengaged, the processor 50 advances to return step 214 and returns to start 202.

Returning to decision step 210 shown in FIG. 11, when the processor 50 determines that the power increase actuator 60 is not enabled, the routine 200 advances to decrease power level decision step 216. At decision step 216, the processor 50 determines if the power decrease actuator 56 is enabled. When the power decrease actuator 56 is enabled, the probe routine 200 advances to step 218. At step 218, the power level value for the cutting operation is decreased by a discrete power level value. When the decrease actuator 56 is disabled, the routine 200 advances to return step 220 and then returns to start step 202.

Figure 12:
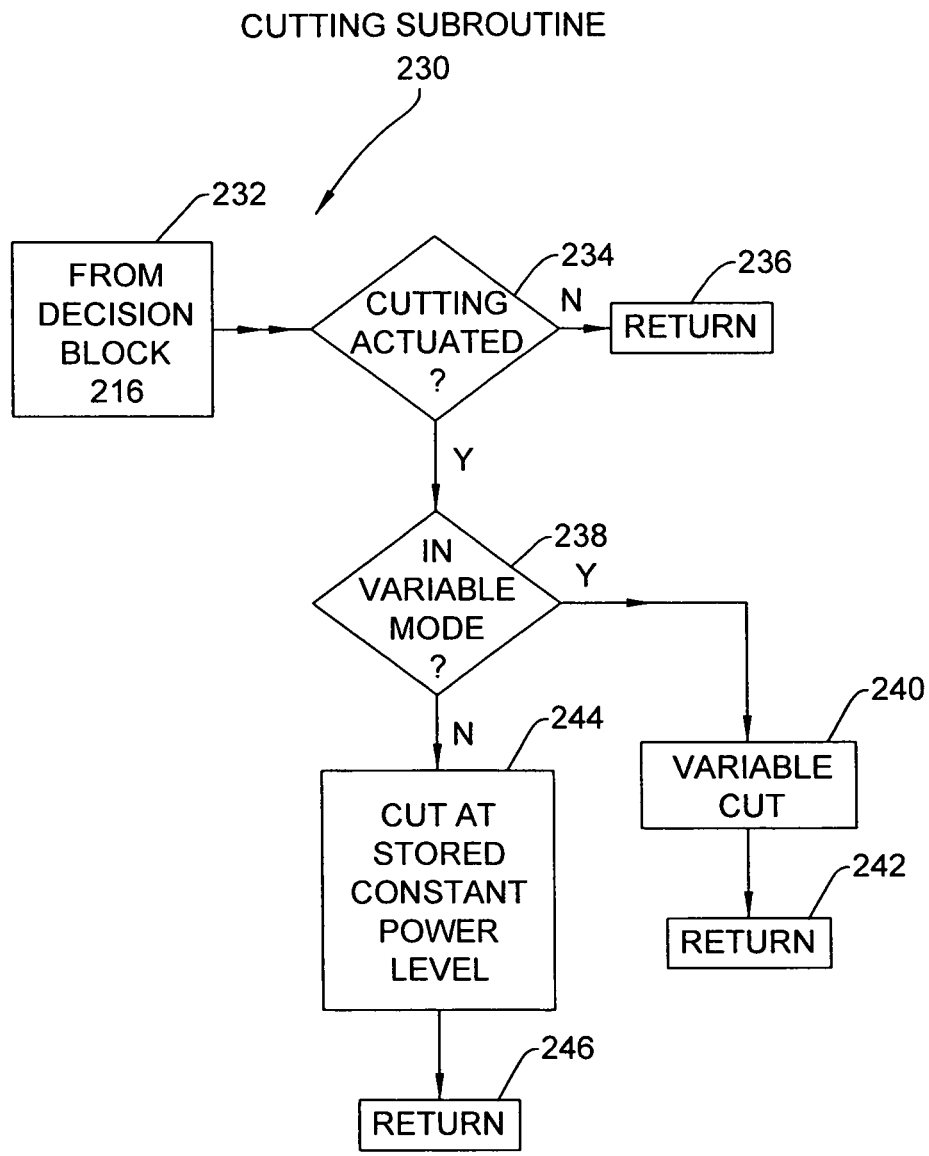
FIG. 12 is a flow chart of a cutting subroutine for the embodiment of FIG. 11.

Returning to decision step 216, when the power decrease actuator 56 is not enabled, the electrosurgical probe routine 200 advances to cutting subroutine 230 shown in FIG. 12. The cutting subroutine 230 begins at block 232 shown in FIG. 12 which represents a NO output from decision step 216 of the electrosurgical probe routine 200 shown in FIG. 11.

In the cutting subroutine 230, the processor 50 advances from block 232 to cutting decision step 234. At decision step 234, the processor 50 determines if the cutting actuator 62 is enabled. When the cutting actuator 62 is not enabled, the processor 50 advances to return step 236 and returns to start step 202 illustrated in FIG. 11.

When the cutting actuator 62 is actuated, the processor 50 advances from cutting decision step 234, to variable mode decision step 238. At decision step 238, the processor 50 determines if the electrosurgical probe arrangement is set in the variable operating mode.

In some embodiments, variable mode is preset for the console as a user preference at start up of the control console 32. As discussed above, in some embodiments the power increase actuator 60 selects the variable mode. In other embodiments, a separate actuator (not shown) selects between the variable and fixed operating mode for the electrosurgical probe 44.

At the variable mode decision step 238, when the processor 50 determines that the variable mode has been set or selected, the cutting subroutine 230 advances to variable cut step 240 to provide a variable power output from the RF generator 52 to the electrosurgical probe 44 so long as the cutting actuator 62 is operated.

As discussed in the first embodiment shown in FIGS. 6, 7 and 9, the cutting power actuator 62 can vary the power from a low value to a maximum value based upon measurement of the force applied thereto. In another embodiment, movement of the actuator 62 against a biasing device, such as a spring element, controls the amount of power supplied from the RF generator 52 to the electrosurgical probe 44. In some embodiments, the power decrease actuator 58 and the power increase actuator 60 can select a maximum power value for use during variable operation of the electrosurgical probe 44.

When the cutting power actuator 62 is disabled, power output by the RF generator 52 is discontinued and the processor 50 advances to return step 242. At step 242, the cutting subroutine 230 returns to start block 202 of the probe routine 200 illustrated in FIG. 11.

Returning to decision step 238, when the processor 50 determines the electrosurgical arrangement is not in the variable mode, the processor 50 advances to constant power level cutting step 244. At cutting step 244, the RF generator 52 provides the pre-selected constant power level to the electrosurgical probe 44 until the cutting power actuator 62 is deactivated. After deactivation, the RF generator 52 stops providing power and the processor 50 advances to return step 246. At step 246, the cutting subroutine 230 returns to start step 202 of the probe routine 200 illustrated in FIG. 11.

Alternatives

While the above embodiments disclose a specific control pattern or function for each of the actuators 56, 58, 60, 62, 64 on the controller 40, which in this embodiment is a foot controller, other embodiments of actuators provided on a controller 40 are contemplated. In some embodiments, the actuators are repositioned or the functions of specific individual actuators on a foot controller can be changed.

As set forth above, the actuator 62 enables power to the electrosurgical probe 44 in both a variable mode and a fixed mode. Thus, the actuator 62 may be considered a variable/fixed mode power actuator. In some embodiments, other actuators provide the same, different, or multiple functions.

While FIGS. 4 and 5 only show a foot operated controller 40, other embodiments are contemplated. For instance, the electrosurgical probe 44 illustrated in FIG. 3 may have a grouping of three or more actuators disposed thereon that perform essentially the same functions as the actuators on the foot controller 40. Further, in another embodiment, the actuators illustrated in FIG. 5 are provided as control buttons on the control console 32 as illustrated in FIG. 3.

In some embodiments, various actuators disposed on the controller 40 or disposed on the electrosurgical probe 44 may perform similar functions or share control of the electrosurgical probe. In one embodiment, an operator utilizes the foot controller 40 to select a variable power cutting mode or a fixed power cutting mode. Then, one of the actuators on the electrosurgical probe 44 shown in FIG. 3 is operated to provide various discrete power levels to the electrode 46 in a similar manner as the actuators disposed on the foot controller 40.

In some embodiments the control console 32 provides an audible and/or visual indication of the selected device and the selected mode.

While FIGS. 2 and 8 disclose power values at various settings, in some embodiments a power value corresponds to an output voltage value that essentially remains constant regardless of the output resistance or load of the electrosurgical probe 44 and the electrode 46. Thus, throughout the instant specification and claims, terms such as discrete power level, power value, fixed power, variable power and the like are intended to include predetermined voltage values or voltage levels output by the RF generator 52.

The routines and subroutines illustrated in FIGS. 6, 7 and 9-12 are for purposes of describing various embodiments of the invention. Additional embodiments of the invention are contemplated wherein the routines and subroutines operate in a different order and/or have additional steps that provide similar operating results as the specific routines and subroutines disclosed herein.

Although particular preferred embodiments of the invention are disclosed in detail for illustrative purposes, it will be recognized that variations or modifications of the disclosed apparatus, including the rearrangements of parts, lie within the scope of the present invention.

What is claimed is:

1. A surgical system comprising:
a console including a processing device;
an RF generator for providing RF energy;
an electrosurgical probe including a cable for connecting to the console;
a powered surgical handpiece with a mechanical cutting tool connected thereto; and
a controller connected to the console for providing a control signal to the processing device, the controller including a plurality of actuators comprising:
a device selection actuator for providing a selection signal to the processing device to select one of the electrosurgical probe to operate in a variable mode and the powered surgical handpiece with the mechanical cutting tool for operation in a tool mode;
a first actuator that is operative in the variable mode to provide a variable control signal to the processing device so that changes in the variable control signal result in the processing device providing a power level signal to the RF generator, the RF generator outputting one of different discrete power levels, the first actuator changing the variable control signal to the processing device in response to force applied thereto so that changes in the variable control signal result in changes in the discrete power level applied to the electrosurgical probe, and the first actuator being operative in the tool mode to provide power to the surgical handpiece,
a second actuator that is operative in the variable mode to provide a substantially constant coagulation power value to the electrosurgical probe, the second actuator being operative in the tool mode to control oscillation or rotation speed of the mechanical cutting tool with the powered surgical handpiece; and
an additional actuator, wherein one of the additional actuator, said first actuator and said second actuator is capable of selecting a fixed mode, and in response to selection of the fixed mode, the additional actuator is operative to change one of the discrete power levels for output from the RF energy generator to the electrosurgical probe only when the first actuator is not providing a variable control signal that results in the output of the discrete power level from the electrosurgical probe.

2. The surgical system of claim 1, wherein the RF energy generator supplies essentially no power to the electrosurgical probe when no force is applied to the first actuator or to the second actuator and the electrosurgical probe is selected.

3. The surgical system of claim 1, wherein the controller comprises a foot controller connected to the console.

4. The surgical system of claim 3, wherein in the variable mode, the power value comprises a plurality of discrete power levels corresponding to a predetermined distance of travel of the first actuator of the foot controller, the highest power level corresponding to the maximum distance of travel of the first actuator of the foot controller, wherein the distance of travel of the first actuator is sensed by a position sensor to provide a position signal based on the amount of actuation thereof to the processing device, and wherein the processing device is configured to correlate distance of travel of the first control actuator of the foot controller to the discrete power levels for output by the RF energy generator.

5. An electrosurgical system comprising:
a console including a processing device;
an RF energy generator for providing RF energy;
an electrosurgical probe including a cable for connecting to the console;
and
a controller connected to the console for providing a control signal to the processing device, the controller configured to selectively operate the electrosurgical probe in a variable mode and in a fixed mode, the controller comprising a plurality of actuators including:
a selection actuator for providing a selection signal to the processing device to select one of the variable mode and the fixed mode for operating the electrosurgical probe;
a power increase adjustment actuator for increasing a power value for the electrosurgical probe in the fixed mode when power is not applied to the electrosurgical probe;
a power decrease adjustment actuator for decreasing a power value for the electrosurgical probe in the fixed mode only when power is not being applied to the electrosurgical probe;
a first control actuator operative in the fixed mode for outputting power at a power value to the electrosurgical probe, and wherein the first control actuator operates in the variable mode to apply power at a power value to the electrosurgical probe that depends on an amount of force applied thereto; and
a second control actuator, operative in both the fixed mode and the variable mode for controlling the RF energy generator to output essentially constant intensity coagulation power to the electrosurgical probe for coagulating target tissue.

6. The electrosurgical system of claim 5, wherein the RF energy generator supplies essentially no power to the electrosurgical probe when no force is applied to the first control actuator or the second control actuator.

7. The electrosurgical system of claim 5, wherein the controller comprises a foot controller connected to the console.

8. The electrosurgical system of claim 7, wherein in the variable mode, the power value comprises a plurality of discrete power levels corresponding to a predetermined distance of travel of the first control actuator of the foot controller, the highest power level corresponding to the maximum distance of travel of the first control actuator of the foot controller, wherein the distance of travel of the first control actuator is sensed by a position sensor to provide a position signal based on the amount of actuation thereof to the processing device, and wherein the processing device is configured to correlate distance of travel of the first control actuator of the foot controller to the discrete power levels for output by the RF energy generator.

9. The electrosurgical system of claim 7, wherein in the variable mode, the power value comprises a plurality of discrete power levels corresponding to the amount of force applied to the first control actuator of the foot controller, wherein the amount of force applied to the first control actuator is sensed by a force sensor to provide a force signal to the processing device, and wherein the processing device is configured to receive the force signal and correlate applied force from the force sensor of the first control actuator with the discrete power levels for output by the RF energy generator.

10. The electrosurgical system of claim 9, wherein an amount of additional force sensed by the force sensor that is required for advancing from a first discrete power level to an increased second discrete power level is essentially the same amount of additional force as required for advancing from the second discrete power level to a third discrete power level.

11. The electrosurgical system of claim 5, wherein the controller is disposed on the electrosurgical probe.

12. The electrosurgical system of claim 5, wherein the RF energy generator is disposed in the console and the electrosurgical system includes a second separate coagulation actuator mounted on a handpiece for the electrosurgical probe for controlling the RF generator to provide essentially constant intensity coagulation power to the electrosurgical probe.

13. The electrosurgical system of claim 5, comprising a powered surgical handpiece supporting a mechanical cutting tool having a cable for connecting to the console, and comprising a device selection actuator for selecting either the electrosurgical probe or the mechanical cutting tool.

14. An electrosurgical system comprising:
a console including a processing device;
an RF energy generator disposed in the console for providing RF energy;
an electrosurgical probe including a cable for connecting to the console;
and
a controller comprising a foot switch controller connected to the console for providing a control signal to the processing device, the controller configured to selectively operate the electrosurgical probe in a variable mode and in a fixed mode, the controller comprising a plurality of actuators including:
a selection actuator for providing a selection signal to the processing device to select one of the variable mode and the fixed mode for operating the electrosurgical probe;
a power increase adjustment actuator for increasing the power value for the electrosurgical probe in the fixed mode;
a power decrease adjustment actuator for decreasing a power value for the electrosurgical probe in the fixed mode;
a first control actuator operative in the fixed mode for controlling the RF generator to output power at a power value to the electrosurgical probe to enable a user to cut target tissue, and the first control actuator operative in the variable mode for controlling the RF generator to output power at a power value to the electrosurgical probe for enabling a user to cut target tissue, the power value comprising a plurality of discrete power levels corresponding to a predetermined distance of travel of the first control actuator of the foot controller, the highest power level corresponding to a maximum distance of travel of the first control actuator of the foot controller, wherein the distance of travel of the first control actuator is sensed by a position sensor to provide a position signal based on the amount of travel thereof to the processing device, and wherein the processing device is configured to correlate distance of travel of the first control actuator of the foot controller to the discrete power levels for output by the RF energy generator; and
a second control actuator, operative in both the fixed mode and the variable mode for controlling the RF energy generator to output essentially constant intensity coagulation power from the electrosurgical probe for coagulating target tissue.

15. The electrosurgical system of claim 14, wherein the electrosurgical system includes a second separate coagulation actuator mounted on a handpiece for the electrosurgical probe for controlling the RF generator to provide essentially constant intensity coagulation power to the electrosurgical probe.

16. An electrosurgical system comprising:
a console including a processing device;
an RF energy generator disposed in the console for providing RF energy;
an electrosurgical probe including a cable for connecting to the console;
and
a controller comprising a foot switch controller connected to the console for providing a control signal to the processing device, the controller configured to selectively operate the electrosurgical probe in a variable mode and in a fixed mode, the controller comprising a plurality of actuators including:
a selection actuator for providing a selection signal to the processing device to select one of the variable mode and the fixed mode for operating the electrosurgical probe;
a power increase adjustment actuator for increasing the power value for the electrosurgical probe in the fixed mode;
a power decrease adjustment actuator for decreasing a power value for the electrosurgical probe in the fixed mode;
a first control actuator operative in the fixed mode for controlling the RF generator to output power at a power value to the electrosurgical probe to enable a user to cut target tissue, and the first control actuator operative in the variable mode for controlling the RF generator to output power at a power value to the electrosurgical probe for enabling a user to cut target tissue, the power value comprising a plurality of discrete power levels corresponding to an amount of force applied to the first control actuator of the foot controller, wherein an amount of force applied to the first control actuator is sensed by a force sensor to provide a force signal to the processing device, and wherein the processing device is configured to receive the force signal and correlate applied force from the force sensor of the first control actuator with the discrete power levels for output of power by the RF energy generator; and
a second control actuator, operative in both the fixed mode and the variable mode for controlling the RF energy generator to output essentially constant intensity coagulation power from the electrosurgical probe for coagulating target tissue.

17. The electrosurgical system of claim 16, wherein an amount of additional force sensed by the force sensor that is required for advancing from a first discrete power level to an increased second discrete power level is essentially the same amount of additional force as required for advancing from the second discrete power level to a third discrete power level.

* * * * *